United States Patent [19]
Durman et al.

[11] Patent Number: 6,013,052
[45] Date of Patent: Jan. 11, 2000

[54] CATHETER AND PISTON-TYPE ACTUATION DEVICE FOR USE WITH SAME

[75] Inventors: Bernie Durman, Pleasonton; Chris Kunis, San Jose; Robert Woodard, Hayward; Fiona Sander, Los Altos Hills, all of Calif.

[73] Assignee: EP Technologies, Inc., San Jose, Calif.

[21] Appl. No.: 08/923,216

[22] Filed: Sep. 4, 1997

[51] Int. Cl.⁷ .................................................. A61M 37/00
[52] U.S. Cl. .............................................. 604/95; 604/264
[58] Field of Search .................................. 604/95, 20, 53, 604/264, 200; 600/131, 146; 607/96, 98, 113, 115, 116, 122

[56] References Cited

U.S. PATENT DOCUMENTS

5,217,465  6/1993  Steppe ...................................... 606/107
5,656,030  8/1997  Hunjan et al. ............................. 604/95

*Primary Examiner*—Wynn Wood Coggins
*Assistant Examiner*—N. Kent Gring
*Attorney, Agent, or Firm*—Henricks Slavin & Holmes LLP

[57] ABSTRACT

A catheter handle including a handle body defining a longitudinally extending handle aperture, a connector adapted to connect a steering wire to the handle body, a piston located at least partially within the handle aperture and slidable relative to the handle aperture, the piston being adapted to be operably connected to a catheter body, and a biasing element, operably connected to the piston, to bias the piston in the distal direction. As an alternative to the biasing element, or in addition, the catheter handle may also include a steering wire anchor associated with the handle body and including a movable portion operably connected to the proximal portion of the steering wire.

59 Claims, 6 Drawing Sheets

CATHETER AND PISTON-TYPE ACTUATION DEVICE FOR USE WITH SAME

BACKGROUND OF THE INVENTION

1. Field of Invention

The present invention relates generally to catheters and, more particularly, to catheters having piston-type actuators.

2. Description of the Related Art

Catheters, which are in widespread medical use today, allow physicians to gain access into interior regions of the body in a minimally invasive manner. In cardiac treatment, for example, the catheter is steered through a main vein or artery into the region of the heart that is to be treated. Once the catheter is within the desired region, additional steering is required to place the operative element (such as an electrode) carried on the distal portion of the catheter into direct contact with the desired tissue.

Although precise control of catheter movement is of paramount importance in all catheter-based procedures, the need for careful and precise control over the catheter is especially critical during certain procedures concerning tissue within the heart. These procedures, called electrophysiological therapy, are becoming more widespread for treating cardiac rhythm disturbances. Cardiac ablation is one procedure in which ability to precisely bend and shape the distal end of the catheter is especially important. Incremental distal end movements of 1 mm to precisely position ablation electrode(s) are not uncommon and it can take up to an hour to precisely position the catheter tip.

Conventional catheters typically include an elongate, hollow catheter body and a handle secured to the proximal end of the catheter body. Piston-type handles include a thumb-actuated inner piston which can be moved relative to the handle. The piston is connected to the hollow catheter body such that distal movement of the piston forces the catheter body in the distal direction. A steering wire passes through the hollow catheter body. The proximal end of the steering wire is fixedly anchored to the handle, while the distal end of the steering wire is secured to the distal end (or tip) of the catheter body. In many instances, the steering wire is connected to a flat leaf spring located within the distal tip of the catheter body. The flat leaf spring makes the distal tip more flexible than the remaining portion of the catheter body.

When the piston is moved distally, the steering wire pulls on the distal end of the catheter body, thereby causing the distal end of the catheter body to deflect into a curved orientation. Moving the piston proximally allows the catheter body to return to its original orientation. Accordingly, physicians are able to steer the catheter by moving the piston back and forth as the catheter is advanced into the patient. Manipulation of the piston also enables the distal tip to be positioned as desired within the patient. The range of piston motion (or "stroke") corresponds to the distance that the steering wire can be displaced prior to causing the distal end of the catheter to "over curve" or "pigtail." A range of motion of approximately 0.4 inch is typical.

When the distal end of the catheter body is bent, a force is generated that tends to drive the distal end back to its straightened orientation. This force, which is generated by the flat leaf spring, also tends to drive the piston in the proximal direction. In order to hold the piston in various locations along its stroke and prevent the distal end of the catheter body from straightening out when the physician releases the piston, the handle includes a set screw that applies a friction force to the piston. The friction force applied to the piston by the set screw must, of course, be greater than the maximum force generated by the distal end of the catheter body. The maximum force is generated when the piston is in its distal-most position and the distal end of the catheter body is in its most curved orientation. The maximum force generated by the distal end of the catheter body is approximately 4 lbs. in many conventional catheters and the amount of friction force required to hold the piston is, therefore, slightly more than 4 lbs. The distal end force will, of course, be greater is some types of catheters than it will in others, as will the friction force.

Figure 1:
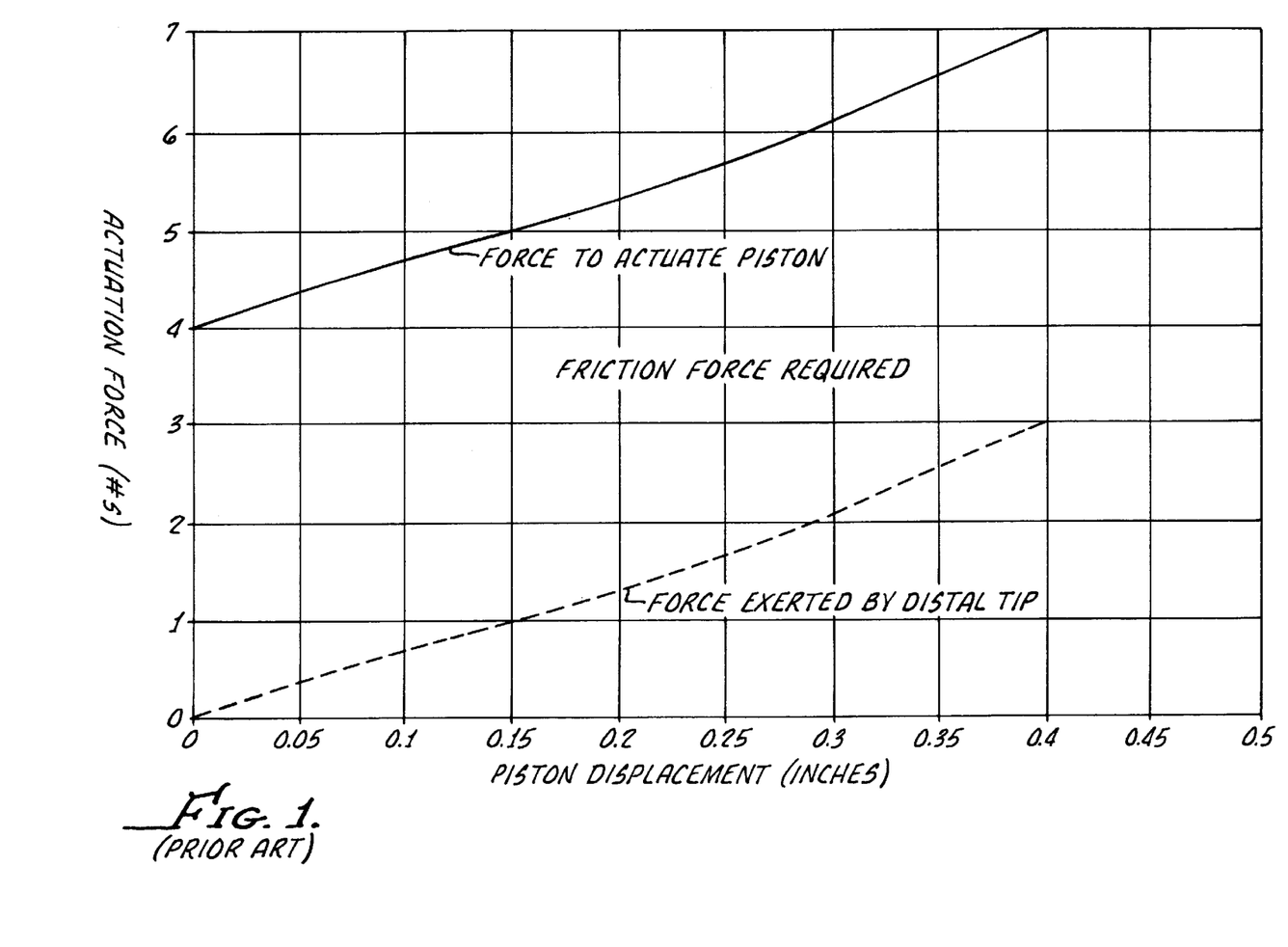
FIG. 1 is a graphical illustration of the forces at work in a conventional piston-type catheter.

Despite the aforementioned need for precise catheter control, the inventors herein have determined that conventional piston-type handles suffer from a number of shortcomings which make it difficult for the physician to precisely control the curvature of the catheter. For example, a relatively large static friction force created by the set screw, as well as the force generated by the leaf spring, must be overcome just to get the piston moving. This phenomenon is illustrated in FIG. 1. As noted above, the physician drives the piston with his or her thumb. Generating an actuation force sufficient to overcome the friction force created by the set screw is not only uncomfortable, it also tends to make movement of the piston unsteady (or jerky). This is especially true when the physician begins to drive the piston from an at rest state to the location corresponding to the next desired distal end curvature. In instances where incremental movements of 1 mm may be required, unsteady movement of the piston often leads to missed targets and adds unnecessarily to the amount of time which it takes to position the catheter.

Figure 11:
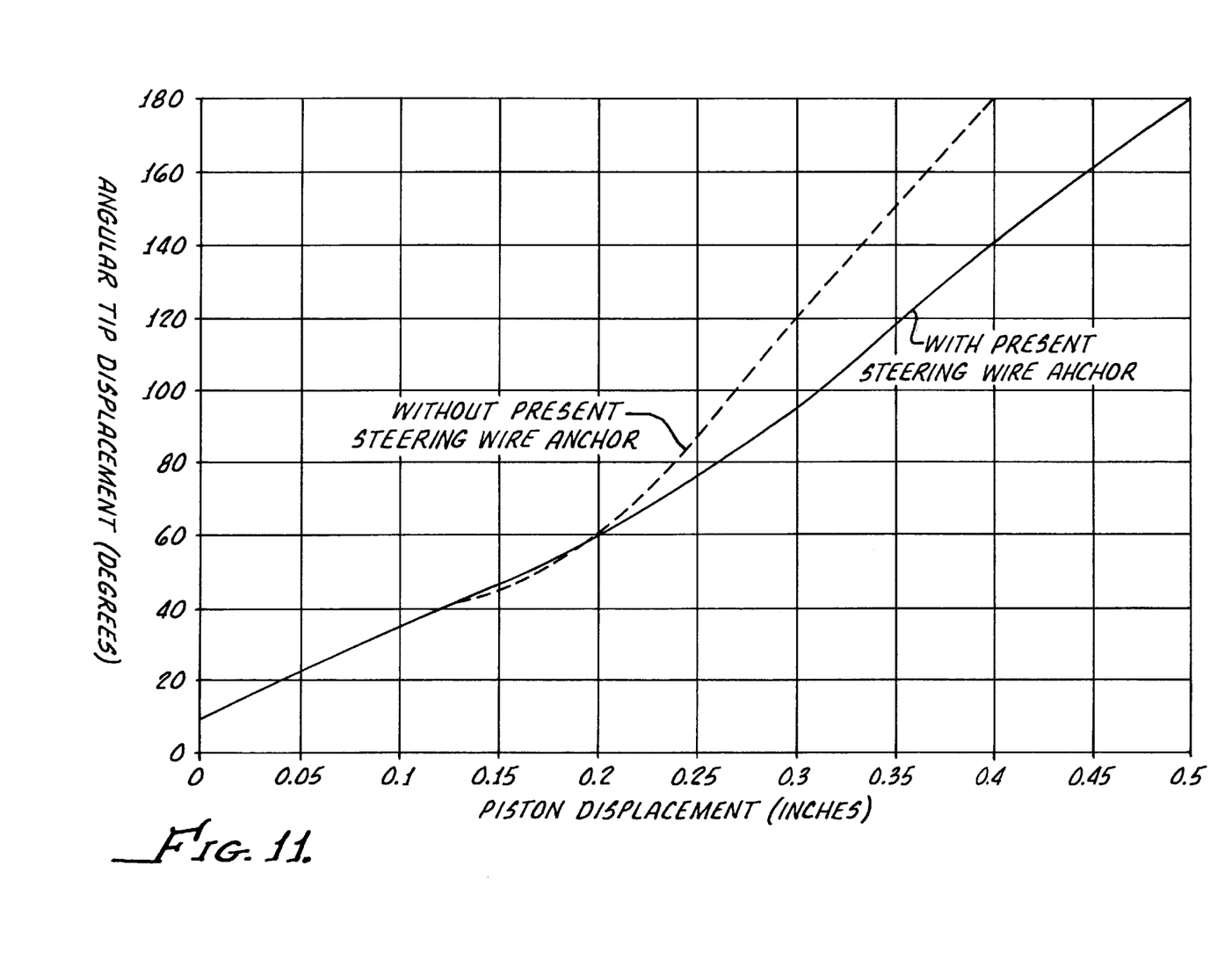
FIG. 11 is a graphical illustration of the relationships between piston movement and tip movement in a conventional catheter and a catheter in accordance with the present invention.

The inventors herein have also determined that another problem associated with conventional piston-type handles is that the displacement of the catheter tip is not linear over the piston stroke. Moving the piston 0.1 inch when the piston is close to its proximal-most position will lead to less distal tip movement than 0.1 inch of piston movement when the piston is close to its distal-most position. In other words, movement of the distal tip accelerates with distally directed movement of the piston and decelerates with proximally directed movement. This phenomenon is illustrated in FIG. 11 in that the relationship between piston displacement and distal tip displacement is non-linear and there is a great disparity between the respective piston displacement to tip displacement relationships at the distal and proximal ends. The inconsistent relationship between piston displacement and distal tip displacement makes it difficult for the physician to accurately position the distal end of the catheter.

Moreover, the actuation force is greatest when the piston is being pushed distally near the distal-most end of the stoke, where the physician's thumb is in the most extended position. This adds to the difficulty associated with the accurate positioning of the distal end of conventional catheters.

The inventors herein have further determined that it would be desirable to increase the stroke of the piston in order to improve control of the catheter tip. Unfortunately, as noted above, the piston stroke in conventional catheters is limited by the distance that the steering wire can be displaced prior to causing the distal end of the catheter to "over curve" or "pigtail."

SUMMARY OF THE INVENTION

Accordingly, the general object of the present invention is to provide a catheter handle which avoids, for practical purposes, the aforementioned problems. In particular, one object of the present invention is to provide a catheter handle which reduces the amount of force (as compared to conventional handles) that the physician must apply to the piston. Another object of the present invention is to provide a catheter handle which provides a consistent relationship between piston movement and distal tip movement. Still another object of the present invention is to provide a catheter handle which extends the stroke of the piston beyond the maximum distance that the steering wire can be displaced.

In order to accomplish some of these and other objectives, a catheter handle in accordance with one embodiment of the present invention includes a biasing element, operably connected to the piston, to bias the piston in the distal direction. The biasing element overcomes a substantial portion of the force that is applied to the piston by the leaf spring. This allows the static friction force created by the set screw to be reduced. Therefore, the actuation force that the physician must generate with his or her thumb is correspondingly reduced. This reduction makes catheters including the present handle more comfortable to use. Additionally, because the amount of force necessary to get the piston moving is reduced, the unsteadiness or jerkiness which is associated with conventional catheters is also reduced.

In order to accomplish some of these and other objectives, a catheter handle in accordance with another embodiment of the present invention includes a steering wire anchor which has a movable portion operably connected to a portion of the steering wire. The movable portion of the steering wire anchor will move a small distance in the distal direction when the piston moves in the distal direction and will move a small distance in the proximal direction when the piston moves in the proximal direction. When the movable portion of the steering wire anchor moves, some of the piston movement is lost. In other words, a portion of the piston's movement is not translated into bending at the distal end of the catheter because the steering wire is displaced with the catheter body. Preferably, more of the piston's movement is lost when the piston is near its distal-most position than when the piston is at its proximal-most position.

There are a number of benefits associated with present steering wire anchor. For example, because more of the piston's movement is lost when the piston is near its distal-most position, the present handle corrects the aforementioned problem associated with the acceleration (or deceleration) of the distal tip. This results in a constant relationship between movement of the piston and movement of the distal tip over the piston's entire stroke. The lost movement also allows the piston in the present handle to have a longer stroke than a conventional handle in a catheter having the same distal tip configuration. The longer stroke provides more precise tip control.

The above described and many other features and attendant advantages of the present invention will become apparent as the invention becomes better understood by reference to the following detailed description when considered in conjunction with the accompanying drawings.

BRIEF DESCRIPTION OF THE DRAWINGS

Detailed description of preferred embodiments of the invention will be made with reference to the accompanying drawings.

DETAILED DESCRIPTION OF THE PREFERRED EMBODIMENTS

The following is a detailed description of the best presently known mode of carrying out the invention. This description is not to be taken in a limiting sense, but is made merely for the purpose of illustrating the general principles of the invention. The scope of the invention is defined by the appended claims.

As illustrated for example in FIGS. 2–5, a catheter 10 in accordance with one embodiment of the present invention includes a hollow, elongate catheter body 12 and a handle 14 consisting partially of a handle body 16 and a piston 18. The piston 18, which is slidably mounted in a longitudinally extending aperture in the handle body 16, includes a thumb rest 20. The handle body 16, piston 18 and thumb rest 20 are preferably formed from machined or molded plastic. One end of a steering wire 22 in the exemplary embodiment is secured to a leaf spring in the distal end 24 of the hollow catheter body 12, while the other end is secured to the handle body 16. The flat steering spring arrangement is discussed in greater detail below with reference to FIGS. 6 and 7.

Figure 2:
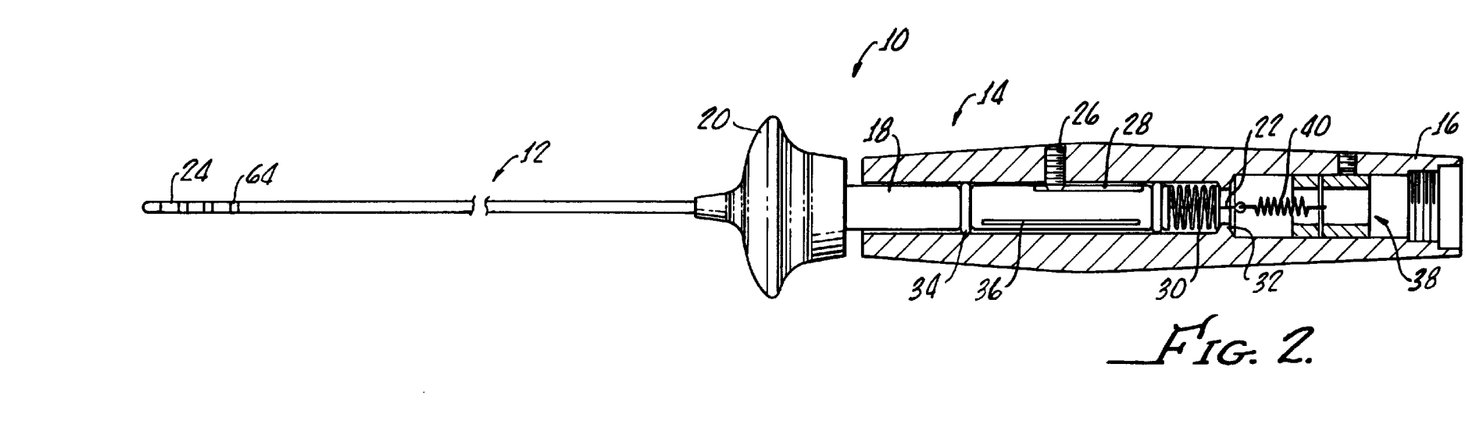
FIG. 2 is a side, partial section view of a catheter in accordance with a preferred embodiment of the present invention with the piston in the fully retracted position.
Figure 3:
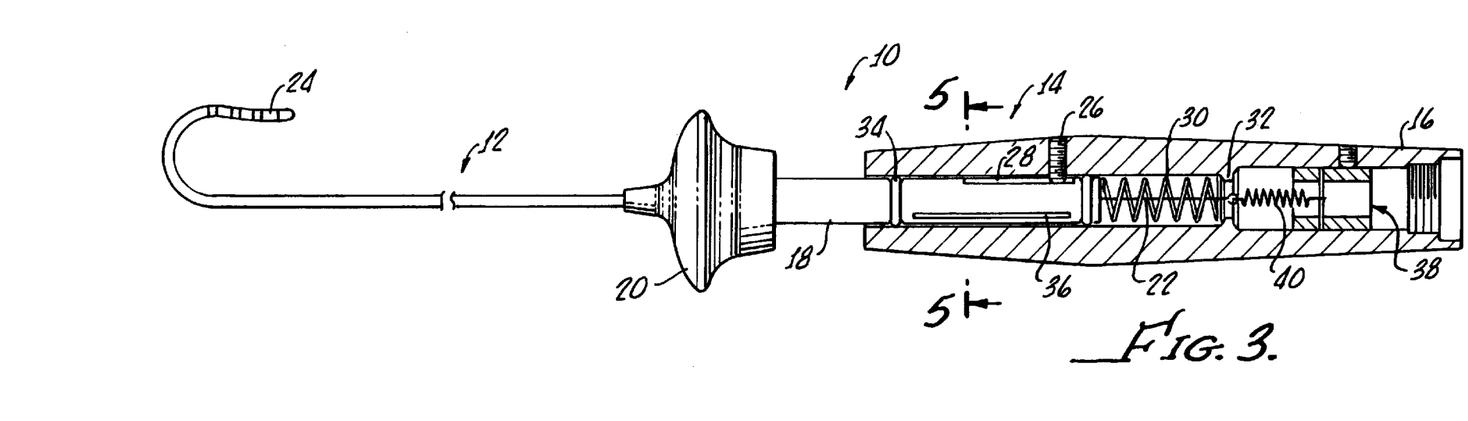
FIG. 3 is a side, partial section view of the exemplary catheter shown in FIG. 2 with the piston in the fully extended position.
Figures 4, 5:
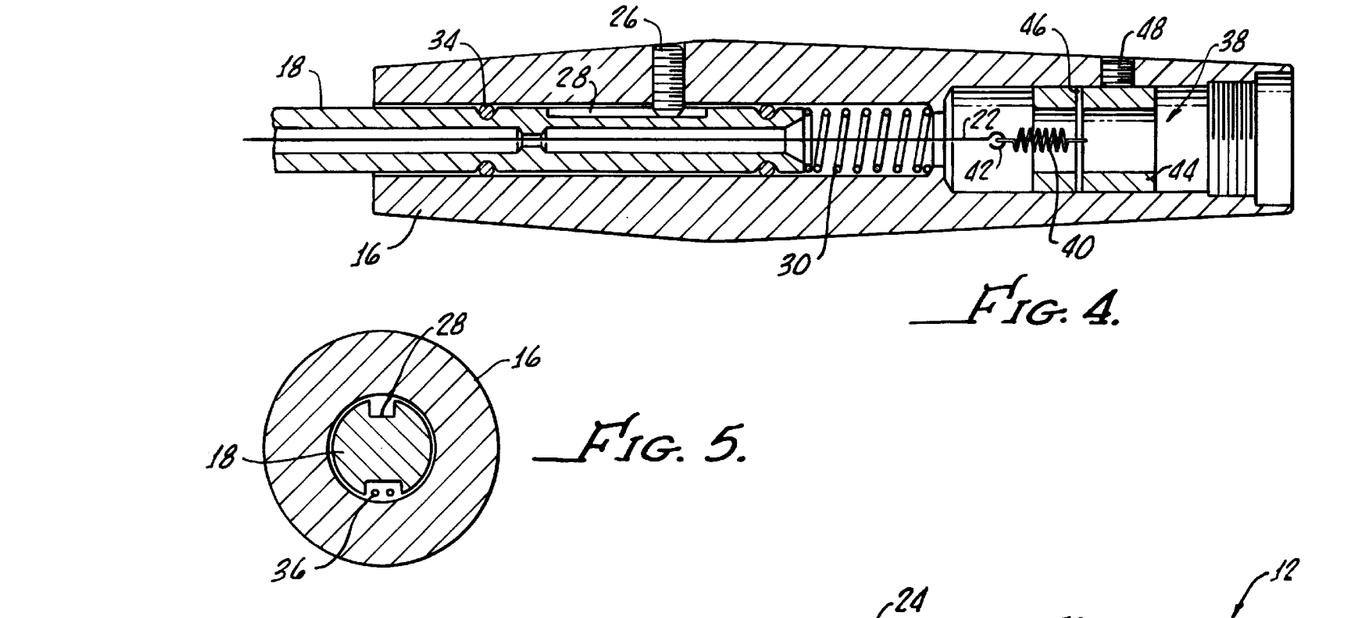
FIG. 4 is a side, partial section view of the catheter handle shown in FIGS. 2 and 3.
FIG. 5 is a section view taken along line 5—5 in FIG. 3.

When the piston is moved distally from the position shown in FIG. 2 to that shown in FIG. 3, the steering wire 22 exerts a pulling force on the distal end 24 of the catheter body 12, thereby causing the distal end of the catheter body to deflect into a curved orientation. Once bent, the coil spring (or steering spring if present) will exert a force on the catheter body 12 that tends to push the piston 18 back into handle body 16 and return the catheter body to the orientation shown in FIG. 2. In the preferred embodiment, this force ranges from 0 lbs. prior to deflection of the catheter to approximately 3 lbs. at maximum deflection.

In order to insure that the piston 18 in the exemplary embodiment does not move once it has been placed in the position corresponding to the desired curvature, a set screw 26 engages a key way 28 formed in the piston. The friction force between the set screw 26 and key way 28 is sufficient to overcome the force generated by a bent coil spring (or steering spring). In the exemplary embodiment, the friction force is approximately 4 lbs. Additionally, the longitudinal edges of the piston key way 28 limit the range of motion of the piston 18 by engaging the set screw 26. In the preferred embodiment, the length of the key way 28 is approximately 0.5 inch, but can range from approximately 0.3 inches to approximately 0.9 inches depending on the configuration of the catheter body. Additionally, although the preferred embodiment includes the above-described set screw and key way arrangement, other mechanisms for applying a friction force to the piston and limiting its range of motion may also be employed. For example, fluting to limit the range of piston motion, a tapered collet, o-rings in addition to those discussed below, or a circumferential piston grip may be used in place of the preferred screw and key way arrangement.

Figure 10:
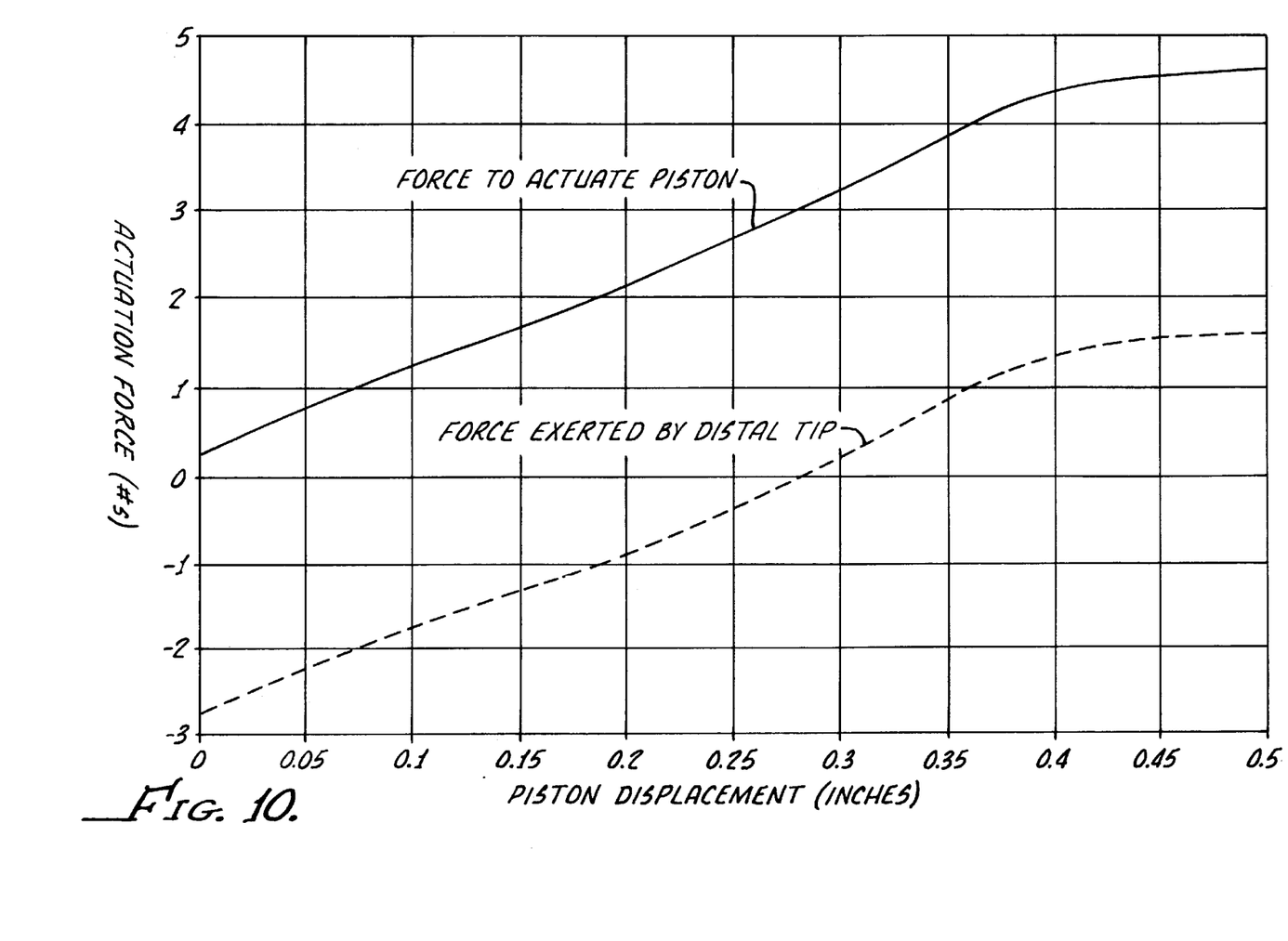
FIG. 10 is a graphical illustration of the forces at work in one example of a catheter in accordance with the present invention.

The catheter 10 also includes a biasing element that applies a distally directed biasing force to the piston 18. As shown by way of example in FIG. 10, the biasing force reduces the amount of force that must be applied to the piston 18 by the physician to move the piston in the distal direction. In the preferred embodiment illustrated in FIGS. 2–5, the biasing element is in the form of a compression spring 30 that is located between the proximal end of the piston and an annularly shaped abutment 32. Because of the biasing force imparted to the piston 18 by the biasing element, the amount of physician-generated actuation force required to drive the piston is less than that associated with a conventional catheter handle (assuming the other aspects of the catheter are identical as is the case in the comparison graphs shown in FIGS. 1 and 10).

Alternatively, the biasing element may be in the form of a piston and cylinder arrangement, an electromagnetic device, an air damper or an elastomeric insert.

A pair of o-rings 34 may be used to center the piston 18 within the handle body 16. The o-rings 34 also prevent the piston from canting and provide friction which opposes the force of the leaf spring. Additionally, as shown by way of example in FIGS. 2, 3 and 5, the side of the exemplary piston 18 opposite the key way 28 includes a pair of Teflon rods 36 which ride on the surface of the longitudinally extending aperture in the handle body 16. The Teflon rods 36 provide improved lubricity and prevent the set screw 26 from driving the piston 18 into the surface of the aperture. This assists the physician when making small, incremental adjustments to the distal curve.

The exemplary catheter 10 also includes a steering wire anchor 38 that includes a movable portion connected to the steering wire 22. In the preferred embodiment illustrated in FIGS. 2–5, the movable portion of the steering wire anchor 38 is the free end of an extension spring 40. The free end of the spring 40 may be secured to the steering wire 22 by, for example, a solder joint 42. The exemplary steering wire anchor 38 also includes a cylindrical member 44 which supports a pin 46. The fixed end of the spring 40 is secured to the pin 46. A set screw 48 secures the cylindrical member 44 within the handle body 16.

The exemplary compression spring 30 has a spring rate of 2.75 lbs./inch and may be formed from stainless steel or music wire. The outer diameter is approximately 0.36 inch, the diameter of the wire is approximately 0.026 inch, the solid height is approximately 0.23 inch and the free length is 1.5 inches. The ends of the spring are closed and ground. The exemplary extension spring 40 has a spring rate of 15 lbs./inch, a 2 lbs. initial tension, and may be formed from stainless steel wire, 17-7 steel wire or music wire. The outer diameter is approximately 0.25 inch, the diameter of the wire is approximately 0.037 inch, and the free length is 0.97 inch between the free end loops. Such springs are available under part numbers 71041 and B3-66, respectively, from Century Spring Corporation in Los Angeles, Calif.

When the piston 18 is moved in the distal direction, the extension spring 40 will stretch and the free end of the spring will move in the distal direction. This allows the steering wire 22 to move distally. Similarly, when the piston 18 is moved in the proximal direction, the extension spring 40 will pull the steering wire 22 in the proximal direction. As such, a portion of the piston's movement is lost and will not result in deflection of the distal portion 24 of the catheter body. The amount of the loss increases as the piston 18 moves distally and decreases as the piston moves proximally. Thus, the greatest loss occurs when the piston is at the distal-most portion of the stroke. The amount of the piston movement that will not be translated into bending of the distal end 24 of the catheter (which varies along the piston stroke) is such that tip acceleration and deceleration is substantially eliminated.

Therefore, as shown by way of example in FIG. 11, and in contrast to the conventional catheter also graphically represented in FIG. 11, the relationship between piston movement and tip deflection is substantially constant over the piston stroke. Moreover, the loss of piston movement allows the stroke of the present catheter handle to be longer than that of a conventional handle (assuming the other aspects of the catheter are identical as is the case in the comparison graph shown in FIG. 11).

Figure 6:
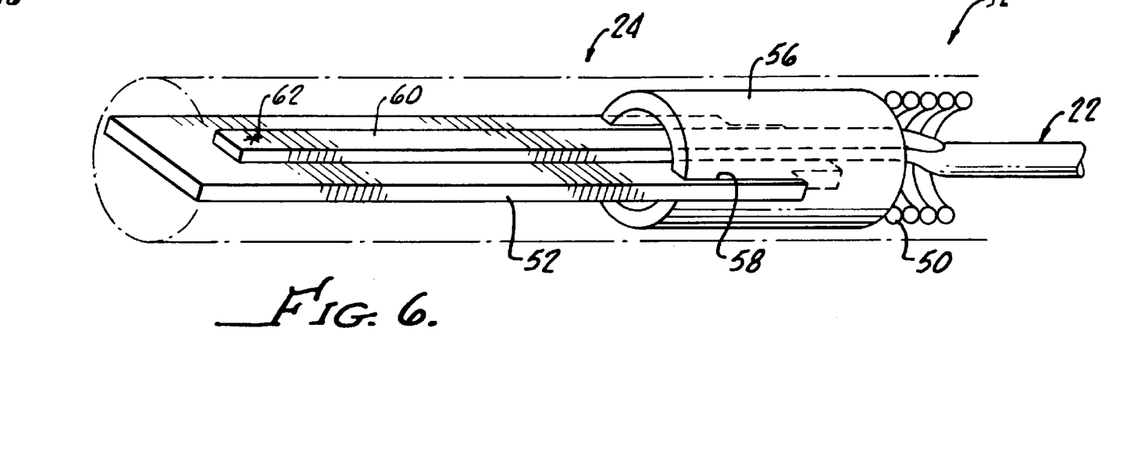
FIG. 6 is a side view of the distal end of a catheter body.
Figures 7, 8, 9:
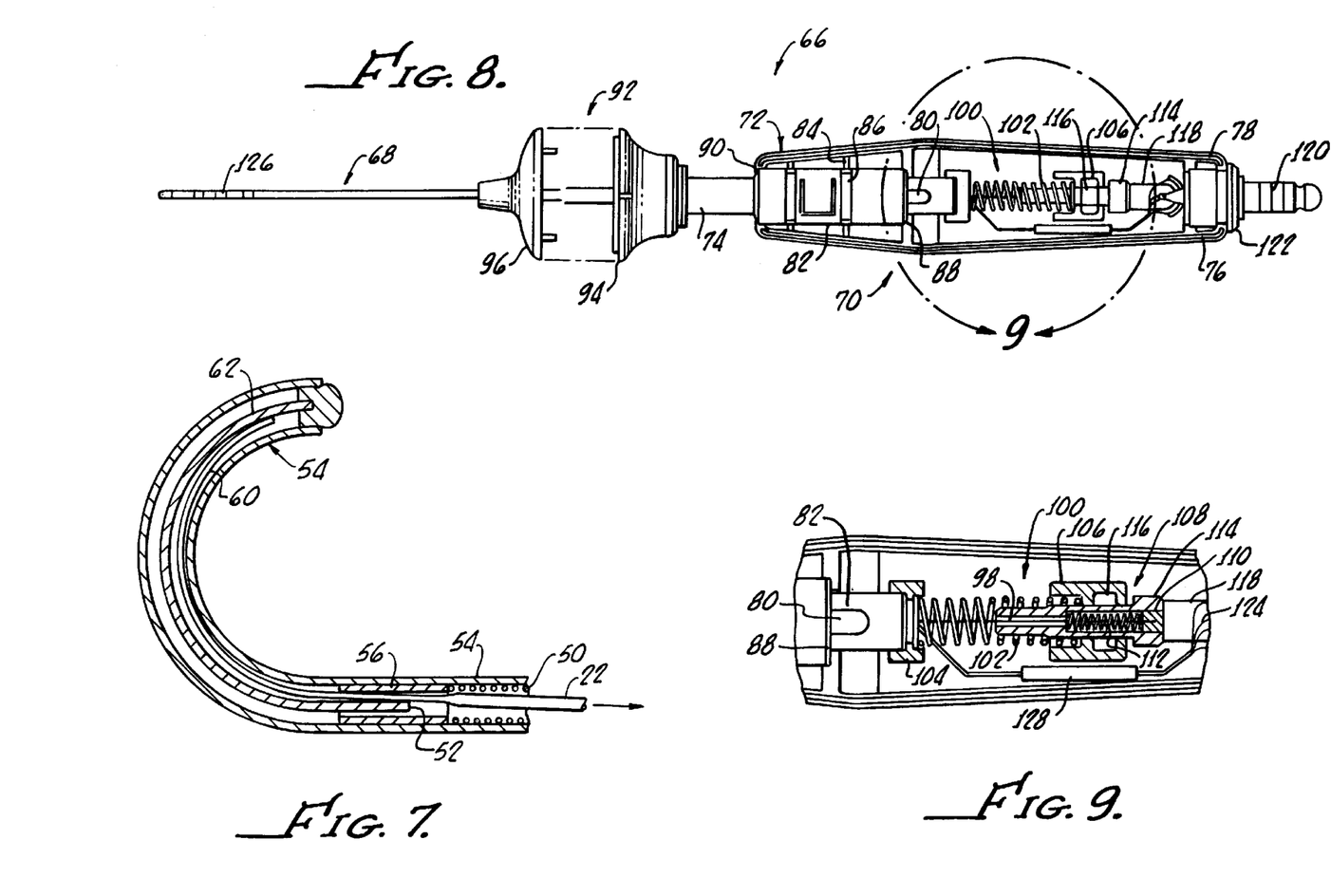
FIG. 7 is a section view of the catheter body shown in FIG. 6.
FIG. 8 is a side, partially exploded view of a catheter in accordance with another preferred embodiment of the present invention with a portion of the handle removed.
FIG. 9 is an enlarged view of a portion of the catheter shown in FIG. 8.

As illustrated for example in FIGS. 6 and 7, the exemplary catheter body 12 may include a coil spring 50 and a steering spring 52 (such as a flat leaf spring) extending from the distal end of the coil spring to the distal tip of the catheter body. Both springs are located within a hollow, flexible catheter tube 54. The stiffness of the steering spring 52 is preferably less than that of the coil spring 50. A ferrule 56 having a slot 58 abuts the coil spring 50 and supports steering spring 52. The distal end 60 of the steering wire 22 is secured to steering spring 52 by, for example, a weld 62. Such a catheter body/steering arrangement is illustrated in U.S. Pat. No. 5,336,182, which is incorporated herein by reference. Other catheter body/steering spring arrangement, such as that shown in U.S. Pat. No. 5,257,451 (which is incorporated herein by reference), may also be employed in conjunction with the present invention.

The exemplary catheter 10 is preferably used for performing ablation procedures and is provided with a plurality of electrodes 64. Catheters which are intended for other use in other procedures are, of course, also within the scope of the present invention.

A catheter in accordance with another preferred embodiment of the present invention is illustrated, for example, in FIGS. 8 and 9. The catheter, which is generally represented by reference numeral 66, includes a catheter body 68 (such as that discussed above with reference to FIGS. 6 and 7) and a handle 70 consisting partially of a handle body 72 and a piston 74. Here, the handle body is preferably a two-part molded plastic assembly (only one of the parts being shown in FIGS. 8 and 9). Each of the parts includes a longitudinally extending protuberance 76 and corresponding slot 78. The slot 78 of one handle part mates with the protuberance 76 of the other during assembly. The piston 74 includes a key way 80 which is engaged by a tab molded onto a rib of the handle body 72. The friction on the piston is created by a set screw extending through the handle body 72 such that it presses on a cantilever tab of a piston supporting cylinder 82. The cantilever tab presses against the piston 74.

In this exemplary embodiment, the piston supporting cylinder 82 is mounted within the handle body 72 through the use of, for example, annularly shaped mounting members 84 and cylinder slots 86. A pair of o-rings 88 and 90 are secured to the respective longitudinal ends of the cylinder 82. The piston 74 is also provided with a thumb rest 92 that preferably consists of a base portion 94 and a cap 96, both of which are formed from molded plastic. Displacement of the distal end of the catheter body 68 is accomplished by driving the piston 74 distally and proximally. To that end, one end of a steering wire 98 is secured to the handle body 72, while the other end is secured to the distal end of a coil spring or to a leaf spring (FIGS. 6 and 7) in the distal end of the catheter body 68.

The preferred embodiment illustrated in FIGS. 8 and 9 includes a biasing element 100 that applies a distally directed biasing force to the piston 74. The biasing force reduces the amount of force required to move the piston in the distal direction. Here, the biasing element is in the form of a compression spring 102. One end of the compression spring 102 is positioned relative to the piston 74 by an adapter 104 that abuts the proximal end of the piston, while the other end of the compression spring abuts a portion of a support member 106 which is mounted within the handle body 72.

The exemplary compression spring 102 has a spring rate of 3.0 lbs./inch and may be formed from stainless steel or music wire. The outer diameter is approximately 0.31 inch, the diameter of the wire is approximately 0.027 inch, the solid height is approximately 0.38 inch and the free length is 1.31 inches. The ends of the spring are closed. Preferably, the exemplary compression spring 112 has a spring rate of 9.0 lbs./inch and may be formed from stainless steel or music wire. The outer diameter is approximately 0.094 inch, the diameter of the wire is approximately 0.014 inch, and the free length is 0.63 inch. The ends are closed. Such springs are available under part numbers 10294 and 3642, respectively, from Century Spring Corporation in Los Angeles, Calif.

Alternatively, the biasing element 100 may be in the form of a piston and cylinder arrangement, an electromagnetic device, an air damper or an elastomeric insert.

The exemplary catheter 66 illustrated in FIGS. 8 and 9 also includes a steering wire anchor 108 that has a movable portion which is connected to the steering wire 98. Here, the movable portion of the steering wire anchor is an anchor block 110 that abuts the proximal end of a compression spring 112. The anchor block 110 and compression spring 112 are located within a longitudinally extending aperture formed in a housing 114. The distal end of the compression spring 112 abuts the distal end of the housing aperture. Thus, when a force is applied to the steering wire 98 in the distal direction which is sufficient to overcome the resistance of spring 112, the anchor block 110 will slide distally within the aperture in the housing 114.

The resistance of the spring 112 may be adjusted by moving the housing 114 longitudinally relative to the handle body 72 and securing it in place. In the exemplary embodiment, a portion of the exterior of the housing 114 is threaded and a correspondingly threaded nut 116 is secured within the support member 106. Accordingly, rotation of the housing 114 will cause the housing to move relative to the handle body 72 and vary the resistance of the spring 112. Of course, other mechanisms for adjusting the location of the housing 114, such as cams, pins and ratchets, may also be used. A cap 118 may be provided on the proximal end of the housing 114.

When the piston 74 is moved in the distal direction, the compression spring 112 will compress and the anchor block 110 will move in the distal direction to allow the steering wire 98 to move distally. Proximally directed movement of the piston 74 allows the spring 112 to push the anchor block 110 (and steering wire 98) in the proximal direction. Here too, a portion of the piston's movement is lost and will not result in deflection of the distal portion of the catheter body 68 which, in turn, prevents some of the movement of the piston from being translated into bending movement of the distal portion of the catheter body. The amount of the loss varies with movement of the piston along its stroke (the greatest loss being at the distal portion of the stroke) so that tip acceleration and deceleration are substantially eliminated.

With respect to electrical connection to a power and control apparatus, each of the exemplary embodiments 10 and 66 may include the exemplary structure shown in FIGS. 8 and 9. More specifically, a connector plug 120 and adapter 122 arrangement is inserted into the proximal end of the handle body 72. A plurality or wires extend from the connector plug 120 to respective electrodes 126 on the catheter body 68. An isolated/insulated signal wire pass-through 128 is also provided.

Although the present invention has been described in terms of the preferred embodiment above, numerous modifications and/or additions to the above-described preferred embodiments would be readily apparent to one skilled in the art. By way of example, but not limitation, distal tip steering mechanisms other than the exemplary leaf spring arrangement may be employed. It is intended that the scope of the present invention extends to all such modifications and/or additions and that the scope of the present invention is limited solely by the claims set forth below.

We claim:

1. A catheter, comprising:
    a handle body defining a longitudinally extending handle aperture;
    a piston located at least partially within the handle aperture and slidable relative to the handle aperture;
    a biasing element, operably connected to the piston, to bias the piston in the distal direction;
    a hollow catheter body defining a distal portion and a proximal portion, the proximal portion of the catheter body being operably connected to the piston; and
    a steering wire within the catheter body defining a distal portion and a proximal portion, the distal portion of the steering wire being operably connected to the distal portion of the catheter body and the proximal portion of the steering wire being operably connected to the handle body.

2. A catheter as claimed in claim 1, wherein the biasing element is located within the handle body.

3. A catheter as claimed in claim 2, wherein the biasing element comprises a spring.

4. A catheter as claimed in claim 1, wherein the piston defines a proximal end and the biasing element applies a biasing force to the proximal end of the piston.

5. A catheter as claimed in claim 4, wherein the handle body includes an abutment within the longitudinally extending aperture and the biasing element is located between the abutment and the proximal end of the piston.

6. A catheter as claimed in claim 5, wherein the abutment comprises an annularly shaped member.

7. A catheter as claimed in claim 1, wherein the piston and longitudinally extending aperture define a predetermined frictional force therebetween, the biasing element applies a predetermined biasing force to the piston, and the biasing force is less than the friction force.

8. A catheter as claimed in claim 1, wherein the biasing element comprises a spring.

9. A catheter as claimed in claim 1, wherein the piston includes at least two longitudinally spaced o-rings.

10. A catheter as claimed in claim 1, wherein the piston defines a surface and a key way formed in the surface and the handle body includes a stop member extending into the key way.

11. A catheter as claimed in claim 10, wherein the key way defines respective longitudinal end portions which cooperate with the stop member to limit movement of the piston relative to the handle body.

12. A catheter as claimed in claim 1, further comprising:
a steering spring located within the distal portion of the hollow catheter body, the distal portion of the steering wire being connected to the steering spring.

13. A catheter as claimed in claim 1, further comprising:
a steering wire anchor associated with the handle body and including a movable portion, the proximal portion of the steering wire being operably connected to the movable portion of the steering wire anchor.

14. A catheter as claimed in claim 13, wherein the steering wire anchor comprises an extension spring.

15. A catheter as claimed in claim 13, wherein the steering wire anchor comprises a compression spring.

16. A catheter, comprising:
a handle body defining a longitudinally extending handle aperture;
a piston located at least partially within the handle aperture and slidable relative to the handle aperture;
a hollow catheter body defining a distal portion and a proximal portion, the proximal portion of the catheter body being operably connected to the piston;
a steering wire within the catheter body defining a distal portion and a proximal portion, the distal portion of the steering wire being operably connected to the distal portion of the catheter body; and
a steering wire anchor associated with the handle body and including a movable portion operably connected to the proximal portion of the steering wire.

17. A catheter as claimed in claim 16, wherein the movable portion of the steering wire anchor is biased in the proximal direction.

18. A catheter as claimed in claim 16, wherein the steering wire anchor includes a tension device having a portion fixedly secured relative to the handle body and a movable portion movable relative to the handle body.

19. A catheter as claimed in claim 18, wherein the tension device comprises an extension spring.

20. A catheter as claimed in claim 19, wherein the handle body includes an extension spring mounting device located within the handle body and the fixed portion of the extension spring is secured to the extension spring mounting device.

21. A catheter as claimed in claim 16, wherein the steering wire anchor includes a compression device having a first portion fixedly secured relative to the handle body and a second portion movable relative to the handle body.

22. A catheter as claimed in claim 21, wherein the compression device includes a compression device housing defining a longitudinally extending aperture and a distal end surface, a compression spring defining a distal end abutting the housing distal end surface and a proximal end, and an anchor member secured to the proximal portion of the steering wire and abutting the proximal end of the compression spring.

23. A catheter as claimed in claim 22, wherein the compression device housing is adapted to be fixedly secured in a plurality of longitudinally spaced locations.

24. A catheter as claimed in claim 23, wherein the compression device housing and handle body comprise respective cooperative threads.

25. A catheter as claimed in claim 16, further comprising a biasing element, operably connected to the piston, to bias the piston in the distal direction.

26. A catheter as claimed in claim 16, wherein the piston includes at least two longitudinally spaced o-rings.

27. A catheter as claimed in claim 16, wherein the piston defines a surface and a key way formed in the surface and the handle body includes a stop member extending into the key way.

28. A catheter as claimed in claim 27, wherein the key way defines respective end portions which cooperate with the stop member to limit movement of the piston.

29. A catheter as claimed in claim 16, further comprising:
a steering spring located within the distal portion of the hollow catheter body, the distal portion of the steering wire being connected to the steering spring.

30. A catheter as claimed in claim 16, wherein the movable portion of the steering wire anchor is operably connected to the proximal portion of the steering wire.

31. A catheter handle for use with catheter including a hollow catheter body defining a distal portion and a proximal portion and a steering wire defining a distal portion operably connected to the distal portion of the catheter body and a proximal portion, the catheter handle comprising:
a handle body defining a longitudinally extending handle aperture;
a connector adapted to connect the steering wire to the handle body;
a piston located at least partially within the handle aperture and slidable relative to the handle aperture, the piston being adapted to be operably connected to the catheter body; and
a biasing element, operably connected to the piston, to bias the piston in the distal direction.

32. A catheter handle as claimed in claim 31, wherein the biasing element is located within the handle body.

33. A catheter handle as claimed in claim 32, wherein the biasing element comprises a spring.

34. A catheter handle as claimed in claim 31, wherein the piston defines a proximal end and the biasing element applies a biasing force to the proximal end of the piston.

35. A catheter handle as claimed in claim 34, wherein the handle body includes an abutment within the longitudinally extending aperture and the biasing element is located between the abutment and the proximal end of the piston.

36. A catheter handle as claimed in claim 35, wherein the abutment comprises an annularly shaped member.

37. A catheter handle as claimed in claim 31, wherein the piston and longitudinally extending aperture define a predetermined frictional force therebetween, the biasing element applies a predetermined biasing force to the piston, and the biasing force is less than the friction force.

38. A catheter handle as claimed in claim 31, wherein the biasing element comprises a spring.

39. A catheter handle as claimed in claim 31, wherein the piston includes at least two longitudinally spaced o-rings.

40. A catheter handle as claimed in claim 31, wherein the piston defines a surface and a key way formed in the surface and the handle body includes a stop member extending into the key way.

41. A catheter handle as claimed in claim 40, wherein the key way defines respective longitudinal end portions which cooperate with the stop member to limit movement of the piston relative to the handle body.

42. A catheter handle as claimed in claim 31, wherein the connector comprises a steering wire anchor associated with the handle body and including a movable portion, the proximal portion of the steering wire being operably connected to the movable portion of the steering wire anchor.

43. A catheter handle as claimed in claim 42, wherein the steering wire anchor comprises an extension spring.

44. A catheter handle as claimed in claim 42, wherein the steering wire anchor comprises a compression spring.

45. A catheter handle for use with catheter including a hollow catheter body defining a distal portion and a proximal portion and a steering wire defining a distal portion operably connected to the distal portion of the catheter body and a proximal portion, the catheter handle, comprising:

a handle body defining a longitudinally extending handle aperture;

a piston located at least partially within the handle aperture and slidable relative to the handle aperture; and a steering wire anchor associated with the handle body and including a movable portion operably connected to the proximal portion of the steering wire and a fixed portion that is substantially immovable relative to the handle body.

46. A catheter handle as claimed in claim 45, wherein the steering wire anchor includes a compression device having a first portion fixedly secured relative to the handle body and a second portion movable relative to the handle body.

47. A catheter handle as claimed in claim 46, wherein the compression device includes a compression device housing defining a longitudinally extending aperture and a distal end surface, a compression spring defining a distal end abutting the housing distal end surface and a proximal end, and an anchor member secured to the proximal portion of the steering wire and abutting the proximal end of the compression spring.

48. A catheter handle as claimed in claim 47, wherein the compression device housing is adapted to be fixedly secured in a plurality of longitudinally spaced locations.

49. A catheter handle as claimed in claim 48, wherein the compression device housing and handle body comprise respective cooperative threads.

50. A catheter handle as claimed in claim 45, further comprising:

a biasing element, operably connected to the piston, to bias the piston in the distal direction.

51. A catheter handle as claimed in claim 45, wherein the piston includes at least two longitudinally spaced o-rings.

52. A catheter handle as claimed in claim 45, wherein the piston defines a surface and a key way formed in the surface and the handle body includes a stop member extending into the key way.

53. A catheter handle as claimed in claim 52, wherein the key way defines respective end portions which cooperate with the stop member to limit movement of the piston.

54. A catheter handle as claimed in claim 45, wherein the steering wire anchor includes a biasing element.

55. A catheter handle as claimed in claim 54, wherein the biasing element includes a first end defining at least part of the movable portion of the steering wire anchor.

56. A catheter handle for use with catheter including a hollow catheter body defining a distal portion and a proximal portion and a steering wire defining a distal portion operably connected to the distal portion of the catheter body and a proximal portion, the catheter handle, comprising:

a handle body defining a longitudinally extending handle aperture;

a piston located at least partially within the handle aperture and slidable relative to the handle aperture and a steering wire anchor associated with the handle body and including a movable portion operably connected to the proximal portion of the steering wire, the movable portion of the steering wire anchor being biased in the proximal direction.

57. A catheter handle for use with catheter including a hollow catheter body defining a distal portion and a proximal portion and a steering wire defining a distal portion operably connected to the distal portion of the catheter body and a proximal portion, the catheter handle, comprising:

a handle body defining a longitudinally extending handle aperture;

a piston located at least partially within the handle aperture and slidable relative to the handle aperture; and a steering wire anchor associated with the handle body and including a movable portion operably connected to the proximal portion of the steering wire and a tension device having a portion fixedly secured relative to the handle body and a movable portion movable relative to the handle body.

58. A catheter handle as claimed in claim 57, wherein the tension device comprises an extension spring.

59. A catheter handle as claimed in claim 58, wherein the handle body includes an extension spring mounting device located within the handle body and the fixed portion of the extension spring is secured to the extension spring mounting device.

* * * * *